United States Patent [19]

Blytas

[11] Patent Number: 4,560,812
[45] Date of Patent: Dec. 24, 1985

[54] RECOVERY OF GLYCERINE FROM SALINE WATERS

[75] Inventor: George C. Blytas, Houston, Tex.

[73] Assignee: Shell Oil Company, Houston, Tex.

[21] Appl. No.: 679,773

[22] Filed: Dec. 10, 1984

[51] Int. Cl.[4] .................. C07C 29/80; C07C 29/86; C07C 31/22

[52] U.S. Cl. .................. 568/869; 423/178; 423/206 R

[58] Field of Search ........................ 568/869

[56] References Cited

U.S. PATENT DOCUMENTS

| | | | |
|---|---|---|---|
| 1,078,580 | 11/1913 | Guignard et al. ............ | 568/869 |
| 2,436,209 | 2/1948 | Elgin ............................. | 568/869 |
| 2,444,296 | 6/1948 | Keim et al. .................... | 568/869 |
| 2,479,041 | 8/1949 | Elgin ............................. | 568/869 |
| 4,164,507 | 8/1979 | Blytas et al. .................. | 260/412.5 |

Primary Examiner—J. E. Evans
Attorney, Agent, or Firm—Ronald R. Reper

[57] ABSTRACT

Glycerine is recovered from an aqueous waste stream containing but minor amounts of glycerine by the requested steps of; (1) evaporating, (2) contacting with pentanol, (3) separating precipitated salt, (4) flashing to remove pentanol, and (5) vacuum distillation. This process is particularly useful treating saline waste water resulting from the manufacture of epoxy resins.

7 Claims, 1 Drawing Figure

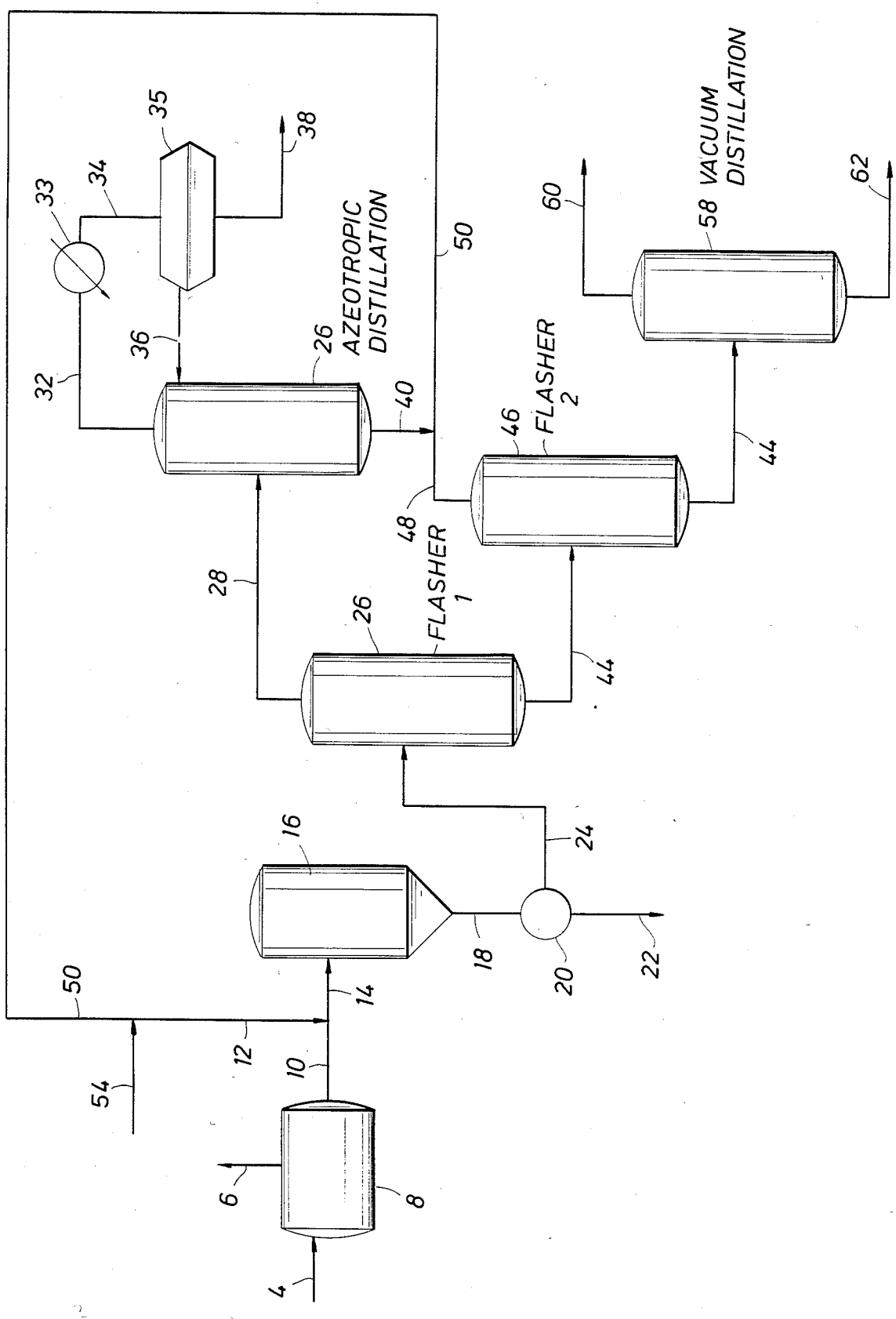

RECOVERY OF GLYCERINE FROM SALINE WATERS

FIELD OF THE INVENTION

This invention relates to a process for the recovery of glycerine from saline water containing glycerine. It is particularly suited for treatment of saline waste water resulting from the manufacture of epoxy resins.

BACKGROUND OF THE INVENTION

Aqueous waste streams containing contaminating amounts of glycerine and polyglycerides are generated in a variety of industrial processes, for example, in the manufacture of epoxy resins. Before such aqueous streams can be discharged into a receiving stream, the organic content must be substantially reduced in order to meet regulatory standards. For example, the production of epoxy resins by reaction of epichlorohydrin and bisphenol may result in an aqueous waste stream containing not only small amounts of glycerine and polyglycerides but in addition inorganic salts of alkali and/or alkaline earth metals. Disposal of such waste streams is both difficult and expensive owing to the presence of the metal salts which engender corrosion/fouling problems for disposal by incineration and of the polyglycerides (telomers of glycerine) which are refractory to biodegradation. Further it is very desirable to recover much of the valuable glycerine.

It is known from my U.S. Pat. No. 4,164,507 to separate salt from the heavy ends wastes of glycerine manufacture consisting of polyglycerides and salt by treatment with n-butanol.

SUMMARY OF THE INVENTION

The invention provides a process for recovering glycerine from a glycerine-containing saline aqueous feed stream which process comprises:

(a) evaporating soil feed stream to remove at least about 90% of the water to precipitate some of the salt content of the said feed stream, to obtain a liquid saline glycerine concentrate stream and precipiated salt, (b) contacting the concentrate stream from step (a) with pentanol consisting substantially of 1-pentanol or a mixture of pentanols at a temperature from about 115°–160° C. in a weight ratio of pentanol to feed from about 1:1 to about 5:1, thereby precipitating a major amount of the salt dissolved in the concentrate stream, and resulting in a liquid concentrate-pentanol mixture, (c) separating the liquid concentrate-pentanol mixture from the precipitated salt, (d) introducing said liquid concentrate-pentanol mixture from step (c) into at least one flash zone to separate an overhead fraction comprising substantially pentanol and a minor amount of water, and a glycerine-containing bottoms fraction, (e) passing at least part of the overhead from step (d) through a water-removal step to obtain a drier overhead fraction having substantially lower water content than the overhead fraction from step (d), (f) recycling the drier overhead fraction from step (e) to said contacting step (b), (g) and distilling by vacuum fractionation distillation the bottoms fraction from step (d) to obtain glycerine as an overhead fraction.

THE DRAWING

The FIGURE depicts a schematic flow diagram of a preferred embodiment according to the invention.

DESCRIPTION OF PREFERRED EMBODIMENTS

In accordance with the invention, a saline aqueous stream containing small amounts e.g., from about 1 to about 7% w glycerine is treated to economically recover the glycerine and to substantially reduce problems relating to the disposal of the remainder of the stream. Disposal of such streams containing significant amounts of metal salts of alkali and/or alkali earth metals such as sodium chloride and calcium chloride is both difficult and expensive owing to the presence of minor, but significant amounts of water soluble organic materials such as glycerine. Further, the recovery and sale of valuable glycerine having utility in a wide variety of applications such as alkyds, tobacco, cellophane, drugs and toilet goods, reduces the overall expense related to the disposal problem.

The process is particularly suitable for treating saline waste streams arising from the manufacture of epoxy resins e.g., by reaction of epichlorohydrin and bisphenol A. Such streams typically contain minor amounts e.g., about 1 to about 7%w glycerine together with some glycerine telomers, and significant amounts e.g., up to about 16%w salts of alkali and/or alkaline earth metals. Exemplary salts are the carbonates, chlorides and bromides of metals, such as, sodium, potassium, lithium, calcium and barium. In general, the process uses highly efficient evaporation equipment and procedures to remove water to precipitate a major amount, at least about 85% w of the inorganic salt content. Such evaporation techniques are not part of the invention, but are well known to those skilled in the art. Exemplary techniques include single or multiple effect short tube evaporators (calandrias) which typically operate under vacuum. The most economical selection between single and multiple effect evaporation usually will depend upon the cost of steam and the total evaporative load. Where energy costs are very expensive, the use of steam vapor recompression techniques may be suitably employed.

It is preferred to use vapor compression evaporation methods. Since each stage of such a process is limited as to the extent of water removal, it becomes appropriate to use several stages of vapor compression evaporation in series, or at least one vapor compression unit followed by one or more evaporator effects.

The salt(s) precipitated by evaporation may be separated prior to contact with pentanol or after contact with the pentanol as desired. Ordinarily, the liquid phase after evaporation will have become highly viscous owing to the higher concentration of glycerine and possibly organic materials, such as, glycerine telomers and the like. Advantageously, contact of the total effluent from the evaporation step with pentanol substantially reduces the viscosity of the mixture and simultaneously precipitates additional salt thereby enabling better separation of the salt and in a single step.

The precipitated salt(s) may be separated from the liquid phase by knwon techniques e.g., filtration, centrifugation, decantation and the like, and disposed of as such, or subjected to further treatment, as desired.

According to the invention, the effluent from the evaporation step is contacted with an alkanol stream which is substantially pentanols. Although commercial isomeric mixtures of pentanols are suitable, applicant has achieved the best results when employing primarily (90%w) 1-pentanol. Although in principal other alkanols such as butanols or hexanols could be used, it has been found in treating the aqueous streams according to the invention that the higher solubility/miscibility of these other alkanols could require elaborate recovery steps to prevent undue losses and/or higher, more costly temperatures of operation.

The pentanol contacts and is mixed with the evaporation step liquid slurry effluent in a suifficient quantity to precipitate substantially all of the salt present at a temperature sufficiently high to ensure complete miscibility of the pentanol and the glycerine-containing phase. Generally temperatures in the range from 115° C. and about 160° C. will be sufficient, however, more typically the temperature range for this contacting step is between about 120° and 155° C. The quantity of pentanol necessary to precipitate the salt may vary somewhat depending upon the relative quantities of glycerine, salt, water and other organics present. Generally, substantially complete precipitation of the salt(s) present can be achieved if the pentanol is added to the concentrate stream in a pentanol:effluent weight ratio of about 1:1 to about 5:1, with ratios of about 2.5:1 to about 2.5:1 being preferred. The use of pentanol to concentrate stream weight ratios above 5:1 is possible, of course, however, use of such high ratios adds to the cost of the process both in energy and capital requirements.

The contacting may be carried out by any conventional mixing procedures whereby the pentanol and concentrate stream are placed in intimate contact for a sufficient time to precipitate the salt. Either batch or continuous mixing may be suitably employed, as the salt precipitation occurs very rapidly after the pentanol and stream concentrate are completely mixed. For plant scale operations, continuous contacting procedures such as pipeline or static mixers are preferred. Very suitably the contacting can be carried out in an agitated vessel wherein the pentanol and concentrate stream are added separately or together into the vessel at a location above the vessel bottom, and a mixture of precipitated salt, pentanol and concentrate stream is withdrawn as a slurry from the bottom of the vessel.

After contacting of the pentanol and concentrate stream, the resultant slurry mixture containing the precipitated salt is passed as a slurry to a solid-liquid separation zone wherein the precipitated salt is separated to afford a substantially salt-free liquid concentrate-pentanol mixture.

By use of pentanol, the separation of the precipitated salt may be carried out at a temperature substantially that of the contacing step e.g. from about 115° C. to about 160° C., and preferably from about 120° C. to about 155° C. Conventional solids-liquid separation procedures suitably employed in this step of the process of the invention include centrifugation, gravity separation and filtration. Pressure filtration employing an inert gas such as nitrogen or carbon dioxide and the like may be advantageous in effecting rapid separation of the liquid concentrate-pentanol mixture. Generally the separated salt will have only minor i.e., less than about 10% w, e.g. less than about 5% w organic content and may be disposed of as such, or subjected to further purification as desired.

After separation of the liquid concentrate pentanol mixture from the solid salt precipitate, said liquid mixture is introduced into a flash zone operated at a lower pressure e.g., from about 30 KPa to about 150 KPa to separate an overhead fraction comprising at least a major amount e.g., more than about 75% w of the water present in the liquid mixture feed to the flash zone, together with a substantial portion of the pentanol, and a bottom fraction which is substantially pentanol, glycerine together with some telomers of glycerine, and very minor amounts e.g., less than about 1% w each of water and salt.

The flash zone may comprise one or a plurality of vessels arranged in series flow. The choice of using one, two or more flash vessels will be determined by practical considerations such as utilities costs, capital availability and the like. In one embodiment employing a series of two flash vessels, the overhead fraction from the first vessel is passed to a azeotropic distillation zone wherein the water is separated as an overhead fraction containing about 95% w or more water, and less than about 5% w pentanol. Since the amount of water separated by such azeotropic distillation is very small, the organic content of the removed water can be disposed of directly in conventional biotreatment facilities without causing an undue load for biotreatment. The bottoms from the azeotropic distillation is essentially pentanol which can be recycled back to the contacting step of the process. The bottoms from the first flash vessel are introduced to a second flash vessel wherein the remainder of the pentanol and any previously unremoved water, if any, are taken overhead and recycled to the contacting step of the process. In a preferred mode, the bottoms from the first flash vessel and the overhead fraction from the second flash vessel are combined for recycle to the contacting step of the process.

In an alternate embodiment, the first flash vessel overhead fraction comprising substantially pentanol is condensed by indirect heat exchange and is recycled to contacting zone, alone or in combination with one or more pentanol streams from subsequent drying steps employing phase separation of the pentanol from a lower water fraction. In this embodiment, the bottom from the first flash vessel is cooled further by indirect heat exchange with an external source of coolant to a temperature below about 80° C. and passed on to a phase separation vessel of appropriate size to afford sufficient residence time for complete phase separation i.e., from about 20 minutes to several hours. The upper pentanol phase is then removed from the phase separation vessel, and alone or in combination with the other pentanol stream from the flash zones and subsequent distillation zone, is recycled to the contacting step of the process. The pentanol glycerine-water containing bottoms mixture from the phase splitter is subjected to fractional distillation wherein all of the pentanol and water are separated as an overhead fraction and the bottoms mixture of glycerine, glycerine telomers; and trace amount of salt is passed to a vacuum distillation zone. The overhead fraction from the fractional distillation zone is cooled to a temperature below about 45° C. and passed to a second phase separation zone to complete phase separation. After the second phase separation the upper alcohol phase is recycled to the contacting step of the process, alone or in combination with the pentanol streams from the flashing step and from the first phase separation.

As will be apparent to those skilled, the temperature of the contacting step can be suitably controlled by adjusting the temperature of the pentanol added. Further, in order to compensate for minor pentanol losses through the process, a small amount of pentanol is added along with the recycle pentanol to maintain the desired ratio of pentanol to concentrate in the contacting step of the process. Generally, the make-up pentanol will amount to less than about 3% w of the pentanol added in the contacting step of the process.

The bottoms fraction from the fractional distillation column is then subjected to vacuum fractional distillation to separate primarily glycerine containing minor amounts of glycerine telomers as an overhead fraction which is passed to storage or, if desired, further purification.

The bottoms fraction from the vacuum fractionation distillation zone comprise primarily glycerine telomers and other organics with but very minor amounts of glycerine and salt and can be passed to disposal means such as incineration or wet oxidation without problems arising from salt contamination.

Reference is made to the FIGURE which represents a schematic flow diagram of a preferred embodiment of the present invention wherein glycerine is recovered from a saline aqueous stream the FIGURE does not purport to show conventional instrumentation and valving present in a typical process.

A saline glycerine-containing aqueous feed stream e.g., from the manufacture of epoxy resins by reaction of bisphenol A and epichlorohydrin and containing from about 1 to about 7% by weight of glycerine is introduced via line 4 to evaporation zone 8 wherein about 95% w of the water originally present in the feed stream is removed in stages at temperatures of about 100° C. to about 65° C. and pressures of about 100 KPa to 20 KPa. The water is removed overhead via line 6 to afford a liquid concentrate stream containing precipitated salt and less than about 5% w water. The concentrate stream passed via line 10 is contacted with pentanol added via line 12, at a pentanol concentrate weight ratio of 4:1 and the admixture is passed via line 14 into precipitator 16 at a temperature of about 150° C. to effect precipitation of about at least about 85% w of the salt present in the concentrate stream. After allowing for a residence time sufficient for complete contacting of the conccentrate and pentanol and precipitation of the salt e.g., 5 minutes to 2 hours, the mixture of concentrate stream, pentanol and precipitated salt is removed from the bottom of the precipitator vessel via line 18 in slurry form. The liquid mixture of concentrate and pentanol is then separated from the solid, precipitated salt in a centrifuge and passed via line 24 to a flashing zone comprising 2 consecutive vessels 26 and 46. The salt from centrifuge 20 is removed via line 22 for disposal, or reuse as desired.

The conccentrate-pentanol mixture via line 24 enters first flash vessel 26 operated at a temperature of about 150° C. and a pressure of about 130 KPa thereby separating overhead fraction comprises at least about 80% w of the pentanol, a major amount e.g. more than 90% w of the water present in the stream entering flasher No. 1 and typically less that about 5% w glycerine. The overhead passes via line 28 to a drying zone exemplified by an azeotropic distillation column 30 wherein all of the water is removed as an overhead fraction and the pentanol bottoms which may contain very minor amounts of glycerine is removed as bottoms via line 40, and recycled via lines 50 and 12 to contact additional concentrate in line 10. In a particularly preferred embodiment, the overhead fraction from azeotropic distillation column 30 is passed via line 32, cooler 33 and line 34 into phase separation vessel 35 operated at a temperature of about 40° C. The pentanol upper phase may be recycled to the azeotropic distillation while the lower aqueous phase containing but a very minor amount (<about 5% w) of pentanol can be disposed of directly in conventional biotreatment facilties, or subjected to further purification, as desired.

From flasher vessel No. 1, the bottoms fraction containing primarily glycerine, pentanol, glycerine telomers and very minor amounts of water and salt is passed via line 44 to second flasher vessel 46 operated at a temperature of about 170° C. and a pressure of about 60 KPa. The overhead from flasher vessel 46 consists essentially of all the pentanol and all of the water which remained in the bottom fraction from the first flasher veseel No. 26. The flashed distillate overhead fraction which may contain up to about 3% w water is removed via line 48 and recycled via lines 50 and 12 to the contact step of the process. The residual fraction from the second flasher vessel 46 consisting essentially of glycerine, other organic materials and a very minor amount of salt is passed via line 56 to vacuum distillation zone 58 operated at a vacuum of about 2 to 5 KPa and a bottoms temperature of about 190° C. The glycerine is obtained as overhead vacuum distillate via line 60 and which may contain minor amounts of glycerine-related organic materials. The bottoms fraction from the vacuum distillation column 58 containing only about 2 to 3% w salt is removed via line 62 to disposal further processing, e.g. incineration or wet oxidation, without encountering problems often associated with high salt content.

What is claimed is:

1. A process for recovering glycerine from a glycerine-containing saline aqueous feed stream which comprises:

(a) evaporating said feed stream to remove at least about 90% of the water present in the feed stream to precipate some of the salt content of said feed stream, to obtain a liquid saline glycerine concentrate stream and precipitated salt, (b) contacting the concentrate stream from step (a) with pentanol consisting substantially of 1-pentanol or a mixture of pentanols at a temperature from about 115°–160° C. in a weight ratio of pentanol to feed from about 1:1 to about 5:1, thereby precipitating a major amount of the salt dissolved in the concentrate stream, and resulting in a liquid concentrate-pentanol mixture, (c) separating the liquid concentrate-pentanol mixture from the precipitated salt, (d) introducing said liquid concentrate-pentanol mixture from step (c) into at least one flash zone to separate an overhead fraction comprising substantially pentanol and a minor amount of water, and a glycerine-containing bottoms fraction, (e) passing at least part of the overhead from step (d) through a water-removal step to obtain a drier overhead fraction having substantially lower water content than the overhead fraction from step (d), (f) recycling the drier overhead fraction from step (e) to said contacting step (b), (g) and distilling by vacuum fractionation distillation the bottom fraction from step (d) to obtain glycerine as an overhead fraction.

2. A process as in claim 1 wherein the pentanol stream is substantially 1-pentanol.

3. A process as in claim 1 wherein step (b) the weight ratio of pentanol to feed is in a weight ratio from 2.5:1 to 4.5:1.

4. A process as in claim 1 wherein step (e) this water removal step comprises azeotropic distillation.

5. A process as in claim 1 wherein the saline aqueous feed stream contains from about 1 to about 7% w glycerine.

6. A process as in claim 1, wherein the saline aqueous stream contains from about 2 to about 17% w of inorganic salts of alkali and/or alkaline earth metals.

7. A process as in claim 1 wherein step (d) the flash zone comprises at least two flash vessels arranged in series flow, the bottoms from the first flash vessel is passed as feed to the second flash vessel and the overhead from the first vessel, after passing through said water removal step (e) is combined with the overhead from the second flash zone which is not subjected to a water removal step to form a combined stream, and the combined stream is recycled to contacting step (b).

* * * * *